(12) United States Patent
Akashi et al.

(10) Patent No.: US 7,427,378 B2
(45) Date of Patent: Sep. 23, 2008

(54) ANALYSIS METHOD AND APPARATUS FOR SULFUR COMPONENT USING ULTRAVIOLET FLUORESCENCE

(75) Inventors: Kotaro Akashi, Kyoto (JP); Hitoshi Hirai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 852 days.

(21) Appl. No.: 10/917,903

(22) Filed: Aug. 13, 2004

(65) Prior Publication Data
US 2005/0079625 A1    Apr. 14, 2005

(30) Foreign Application Priority Data
Aug. 13, 2003   (JP) .............................. 2003-293023

(51) Int. Cl.
*G01N 21/76* (2006.01)
*G01N 21/00* (2006.01)
*G01N 33/00* (2006.01)

(52) U.S. Cl. .................. 422/82.08; 422/52; 422/82.05; 436/106; 436/116; 436/122; 436/123; 436/172

(58) Field of Classification Search ........................ None
See application file for complete search history.

(56) References Cited

U.S. PATENT DOCUMENTS

| 4,077,774 A | 3/1978 | Neti et al. |
| 4,272,248 A | 6/1981 | Neti |
| 5,152,963 A * | 10/1992 | Wreyford .................... 422/80 |
| 5,531,105 A | 7/1996 | Leong et al. |

FOREIGN PATENT DOCUMENTS

| JP | 58-10131 | 2/1983 |
| JP | 63-198852 | 8/1988 |
| JP | 7-25678 | 6/1995 |
| JP | 7-191012 | 7/1995 |
| JP | 11-183385 | 7/1995 |
| WO | WO 02/059596 A2 | 8/2002 |
| WO | WO 02/059596 A3 | 8/2002 |

* cited by examiner

*Primary Examiner*—Jill Warden
*Assistant Examiner*—Timothy G Kingan
(74) *Attorney, Agent, or Firm*—Brooks Kushman P.C.

(57) ABSTRACT

An analysis method and analysis apparatus involve analysis for a sulfur component using ultraviolet fluorescence capable of removing the interferential influence of NO with good efficiency and certainty to thereby measure a concentration of only sulfur components such as $SO_2$ and others even in continuous measurement over a long term with a high precision. An analysis method involves analysis for a sulfur component using ultraviolet fluorescence. A sample gas is illuminated with ultraviolet and fluorescence is emitted by the ultraviolet illumination and detected to measure concentrations of sulfur components including at least $SO_2$ in the sample gas. NO, which is an interferential component in the sample gas, is oxidized to nitrogen dioxide, followed by the illuminating of the sample gas with ultraviolet.

13 Claims, 3 Drawing Sheets

ANALYSIS METHOD AND APPARATUS FOR SULFUR COMPONENT USING ULTRAVIOLET FLUORESCENCE

BACKGROUND OF THE INVENTION

1. Field of the Invention

The invention relates to an analysis method for a sulfur component using ultraviolet fluorescence adopted for measuring concentrations of sulfur components including sulfur dioxide (hereinafter referred to as $SO_2$) in a sample gas such as, for example, an automobile emission, and an analysis apparatus used in conducting the method.

2. Background Art

A nondispersive infrared gas analysis method (NDIR method) has conventionally been adopted in general aspects as a measuring method for concentrations of sulfur components such as $SO_2$ in a sample gas such as an automobile emission. In the NDIR method, an inconvenience could not be avoided even if an optical filter is used, because of a low removal percentage of interferential components such as $H_2O$ and HC coexisting with a sulfur component as a measurement objective in a sample gas, the interferential components give an adverse influence on a measurement precision.

In order to eliminate the adverse influence caused by such interferential components (which is hereinafter simply referred to as interferential influence), a necessity arises for installing a greatly expensive pretreatment facility, leading to complexity and scaling-up of the apparatus in the entirety in which $H_2O$ is removed using a Perma-pure drier (PPD) and HC is removed by burning it to convert to $CO_2$ in a high temperature combustion furnace at a temperature in the vicinity of 900° C. with an oxidation catalyst.

Even in a case where such a pretreatment facility is installed, the interferential influence cannot be perfectly removed. Therefore, in addition to the pretreatment facility, another necessity arises for eliminating the interferential influence, for example, by adopting a so-called fluid modulation method (cross-flow) in which a sample gas and a reference gas are alternately introduced into a sample cell at a given period in a given amount, resulting in faults due to not only further increasing a facility cost and scaling-up of the apparatus, but also lacking responsiveness to a sudden change in concentration of a gas to be measured to thereby cause a transient error and in turn, to disable high measurement precision.

As a measuring method for a sulfur component concentration as a replacement for the NDIR method having faults in facility cost and in measurement precision caused by responsiveness to a sudden change in concentration, an analysis method for a sulfur component based on ultraviolet fluorescence has conventionally been already known in which a sample gas is illuminated with ultraviolet to detect an intensity of fluorescence caused by the ultraviolet illumination and measure concentrations of sulfur components including $SO_2$ in the sample gas. Although an analysis method for a sulfur component using ultraviolet fluorescence has a higher ability in selectively measuring only sulfur components such as $SO_2$ to be measured as compared with other analysis methods such as the NDIR method, included in a sample gas is nitrogen monoxide (hereinafter referred to as NO) emitting fluorescence in a similar way to that of a sulfur component to be measured, especially $SO_2$, and NO works as an interferential component in measurement of $SO_2$, leading to a severe interferential influence.

In more detail, in a case of an analysis method for a sulfur component using ultraviolet fluorescence, while illumination is conducted with ultraviolet having a selected wavelength in the vicinity of 220 nm in measurement of $SO_2$, NO included in a sample gas as an interferential component has narrow isolated absorption wavelength regions in the vicinities of wavelengths of 214 nm and 226 nm, which are extremely close to an ultraviolet wavelength for exciting $SO_2$, and fluorescence spectra of $SO_2$ and NO overlap each other to thereby detect an intensity of fluorescence emitted from NO together with that from $SO_2$, resulting in a problem that NO exerts a conspicuous interferential influence on measurement on $SO_2$, which leads to a measurement error.

As an eliminating means for the interferential influence caused by NO, there has been conventionally available a gas filter scheme in which a wavelength selecting section including a gas filter, in which NO is sealed, selectively absorbing light in the vicinities of wavelengths of 214 nm and 226 nm, is installed in an optical path between a light source emitting ultraviolet and a sample chamber of an ultraviolet fluorometric analyzer not to thereby cause NO to be excited and fluoresce (see, for example, JP Publication No. 11-183385).

A subtraction method has been proposed in which provided are: a sample chamber into which a sample gas including $SO_2$ and NO is introduced; and a sample chamber into which a sample gas is introduced by way of a mechanism to remove $SO_2$ with active charcoal; and in addition, two light sources emitting ultraviolet to respective both sample chambers; and two detection sections detecting fluorescence in respective both chamber, wherein a fluorescence amount detected in the latter sample chamber is subtracted from a fluorescence amount detected in the former sample chamber to thereby obtain a fluorescence amount only from $SO_2$ including no interferential influence caused by NO because of the removal (see JP Publication No. 7-63683).

In a case of the gas filter scheme, however, among the above conventional NO interferential influence removal means, an absorption ability of a selected wavelength is reduced by chronological changes in property, condition or the like of a sealed NO gas, and the interferential influence of NO cannot be fully removed through continuous measurement over a long term, which gives birth to a possibility to cause a measurement error.

In a case of the subtraction method, not only are two sets of a sample chamber, a light source and a detection section necessary to be installed, but an arithmetic circuit operating a subtraction is also required, therefore, having led to a problem of complexity and cost-up of the apparatus in the entirety. And furthermore, it takes a considerable time in removal of the interferential influence by applying a subtraction operation on both fluorescence amounts after both fluorescence amounts detected in the two sample chambers are stored and held, having led to another problem of poor measurement efficiency for a $SO_2$ concentration.

SUMMARY OF THE INVENTION

It is an object of the invention to provide an analysis method and analysis apparatus for a sulfur component using ultraviolet fluorescence capable of removing the interferential influence of NO with good efficiency and certainty to thereby measure a concentration of only sulfur components such as $SO_2$ and others even in continuous measurement over a long term with a high precision.

An analysis method for a sulfur component using ultraviolet fluorescence pertaining to the invention is directed to an analysis method for a sulfur component using ultraviolet fluorescence in which a sample gas is illuminated with ultraviolet and fluorescence emitted by the ultraviolet illumination is detected to measure concentrations of sulfur components including at least $SO_2$ in the sample gas, wherein NO, which is an interferential component in the sample gas, is oxidized to nitrogen dioxide (hereinafter referred to as $NO_2$), followed by illuminating the sample gas with ultraviolet.

An analysis apparatus for a sulfur component using ultraviolet fluorescence pertaining to the invention is directed to an analysis apparatus for a sulfur component using ultraviolet fluorescence including: an introducing pipe for a sample gas; and an ultraviolet fluorometric analyzer, connected to the introducing pipe, and illuminating the sample gas with ultraviolet to detect fluorescence emitted accompanying the illumination and to thereby measure concentrations of sulfur components including at least $SO_2$ in the sample gas, wherein means oxidizing NO, which is an interferential component in the sample gas, to $NO_2$ is installed in the introducing pipe part way downstream from the inlet end thereof or immediate after the introducing pipe.

According to an analysis method and analysis apparatus for a sulfur component using ultraviolet fluorescence pertaining to the invention in the preferred embodiment at the detailed level, NO, which is the interferential component included in the sample gas, is oxidized to $NO_2$ exerting no interferential influence before fluorescence emitted by illumination of the sample gas with ultraviolet is detected. Therefore, a concentration of only sulfur components such as $SO_2$ and others to be measured can be obtained without the interferential influence of NO being exerted. Since the interferential influence of NO is removed by oxidation (transformation) of NO to $NO_2$, there occurs essentially no adverse possibility of incomplete or uncertain removal of the interferential influence due to reduction in absorption power for a selected wavelength caused by chronological changes in property and condition of NO gas, which has been experienced in a conventional gas filter scheme, thereby enabling the interferential influence of NO to be removed with certainty even in continuous measurement over a long term to measure concentrations of only sulfur components such as $SO_2$ and others with a high precision at all times. An effect can be exerted that a construction in the preferred embodiment is much simpler as compared with that of the conventional subtraction method; therefore, not only can the apparatus in the entirety be more compact and of lower cost, but the interferential influence of NO can also be removed with good efficiency to thereby greatly improve efficiencies in measurement and analysis of concentrations of a particular sulfur component.

At a more detailed level, the invention comprehends additional features. It is desirable in the invention to adopt means adding ozone into a sample gas as means oxidizing NO to $NO_2$. In this case, an added amount of ozone is controlled according to a change in a NO concentration, which is an interferential component, to thereby enable all NO to be oxidized to $NO_2$ with good efficiency through a reaction of NO included in the sample gas with ozone. And the occurrence of measurement error caused by the interferential influence can be prevented irrespectively of a change in concentration, thereby enabling high precision measurement to be conducted at all times.

In an analysis apparatus for a sulfur component using ultraviolet fluorescence pertaining to the invention, there is preferably provided heating means heating to and holding at a temperature in the introducing pipe of the sample gas and the sample chamber of the ultraviolet fluorometric analyzer in the range where no moisture in the sample is at least condensed to thereby enable condensation of moisture in the sample gas and adsorption of the sulfur components to be prevented. This leads to more improvement on measurement precision of concentrations of sulfur components such as $SO_2$.

In an analysis apparatus for a sulfur component using ultraviolet fluorescence pertaining to the invention, there is preferably a pretreatment section having a first gas line and a second gas line and a valve changing over between flows of the sample gas into the first and second gas lines provided immediately prior to the ultraviolet fluorometric analyzer. Means oxidizing a sulfur compound in the sample gas to sulfur dioxide may be provided in the first gas line. In this case, a flow of the sample gas is changed over into the first gas line to thereby oxidize sulfur compounds such as $H_2S$, $CS_2$ and others in the sample gas to $SO_2$ and to enable a concentration of all the sulfur components in the sample gas to be measured. While on the other hand, a flow of the sample gas is changed over into the second gas line to thereby enable a concentration of only $SO_2$ actually included in the sample gas to be measured. In this way, measurements of concentrations of sulfur components can be individually conducted by changing over between two kinds thereof.

DETAILED DESCRIPTION OF THE PREFERRED EMBODIMENT(S)

Figure 1:
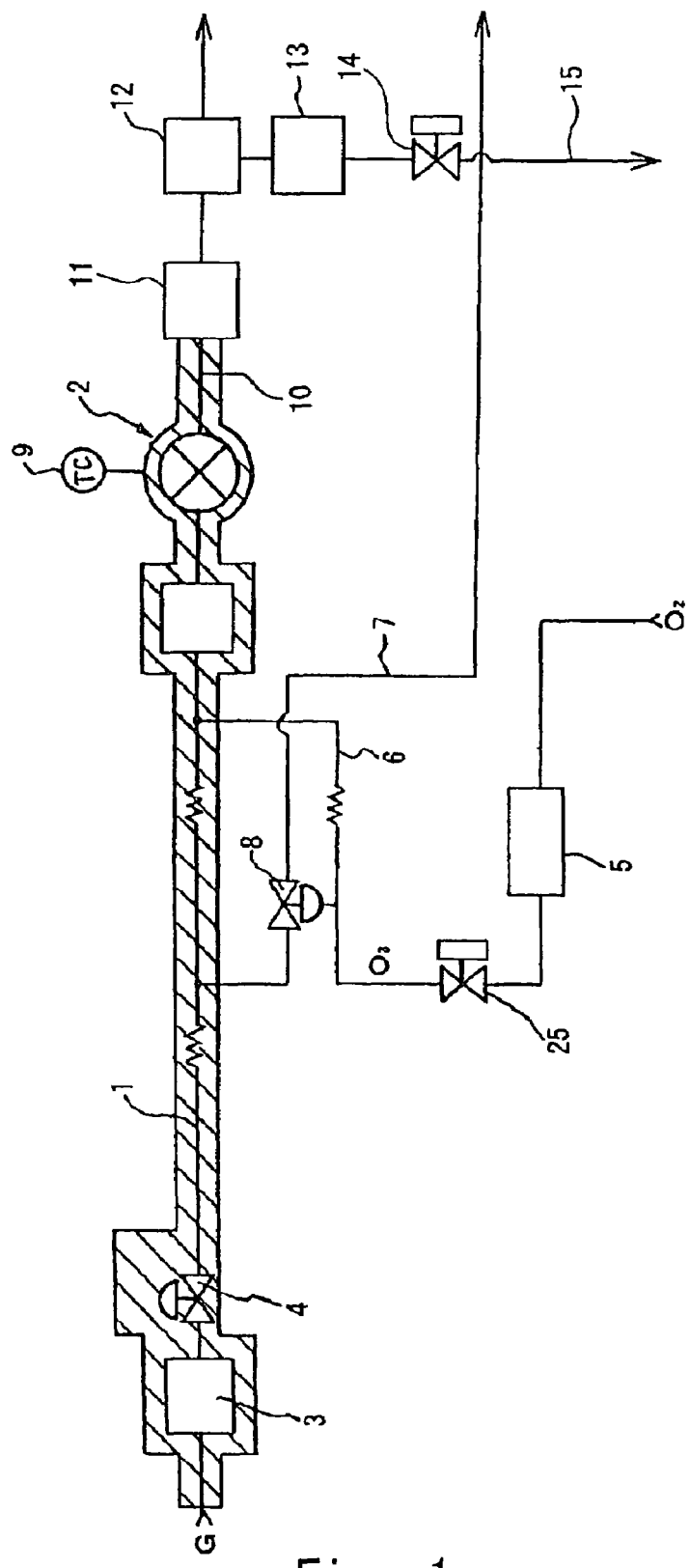
FIG. 1 is a view showing an outline of construction of an analysis apparatus in the entirety according to a first embodiment adopting an analysis method for a sulfur component using ultraviolet fluorescence pertaining to the invention.

FIG. 1 is a view showing an outline of construction of an analysis apparatus in the entirety according to a first embodiment adopting an analysis method for a sulfur component using ultraviolet fluorescence pertaining to the invention. In the figure, a numerical symbol 1 indicates an introducing pipe introducing a sample gas G such as automobile emission including sulfur components such as $SO_2$ to be measured and others, and NO, which is an interferential component, into an ultraviolet fluorometric analyzer 2; and a physical filter 3 removing foreign matter mixed in the sample gas G and a flow rate adjusting valve 4 are inserted in series in the introducing pipe 1 part way downstream from the inlet end thereof. An ozone (hereinafter referred to as $O_3$) supply pipe 6 to which a flow rate adjusting valve 25 capable of adjusting a supply flow rate of $O_3$ generated from pure oxygen (hereinafter referred to as $O_2$) in an ozone generator 5 is attached and is communication-connected to the introducing pipe 1 at a site downstream from the flow rate adjusting valve 4, and $O_3$ is added and mixed into the sample gas G flowing in the introducing pipe 1 through the supply pipe 6 to thereby constitute a means oxidizing NO included in the sample gas G to $NO_2$ through a reaction with $O_3$.

Note that not only is a by-pass pipe 7 discharging the excessive sample gas to the outside connected to the introducing pipe 1 as a branch, but also provided part way downstream from the branching connection of a supply tube 7 is an automatic control valve 8 automatically adjusted with respect to an opening level thereof based on a detected flow rate in the supply pipe 6 for $O_3$. By adjustment in an opening degree of the automatic control valve 8, a flow rate of the sample gas G flowing in the introducing pipe 1, and a flow rate of $O_3$ added and mixed into the sample gas G through the supply pipe 6 are controlled at a constant ratio at all times.

The ultraviolet fluorometric analyzer 2 includes: a sample chamber (cell) into which introduced are the sample gas including $NO_2$ obtained by oxidation of NO and sulfur components such as $SO_2$ to be measured; a light source illuminating the interior of the cell with ultraviolet having a wavelength in the vicinity of 220 nm; and a detector detecting a fluorescent intensity selecting, using an optical filter, fluorescence having a wavelength in the vicinity of 330 nm obtained by excitation caused by ultraviolet illumination; and others, which construction is well known.

The introducing pipe 1 for the sample gas G and the cell of ultraviolet fluorometric analyzer 2 obliquely hatched in FIG. 1 are heated to and held at a temperature at all times by a heating means such as an electrical heater. The heating means is constructed so that a temperature of the sample gas G is controlled in the range of from 110° C. to 120° C. at which neither a moisture in the sample gas G is condensed nor an S compound is adsorbed by current control based on a temperature detected by a thermocouple (TC) 9.

A deozonator 11 decomposing $O_3$ and a drain separator 12 are attached to an exhaust pipe 10 extending from the cell of the ultraviolet fluorometric analyzer 2, and a drain pot 13 and a drain pipe 15 with an opening/closing valve 14 are connected to the drain separator 12.

A method is comprehended for measuring and analyzing a concentration of $SO_2$ included in the sample gas G using ultraviolet fluorescence with the analysis apparatus of the first embodiment constructed as described above. If $O_3$ generated by the ozone generator 5 is added and mixed into the sample gas G including sulfur components such as $SO_2$ to be measured and NO, which is an interferential component, introduced into the introducing pipe 1 and flowing therein, at a constant ratio through the supply pipe 6, NO in the sample gas G reacts with $O_3$ to be oxidized to $NO_2$ and thereafter the sample gas G including $NO_2$ obtained by oxidation is introduced into the cell of the ultraviolet fluorometric analyzer 2. In this situation, the introducing pipe 1 for the sample gas G and the cell of the ultraviolet fluorometric analyzer 2 are heated by means of a heating means such as an electrical heater and further controlled at a temperature in the range of from 110° C. to 120° C. by current control or the like based on a detected temperature by the thermocouple 9. Therefore, neither a moisture in the sample gas G is condensed nor an S compound is adsorbed. Therefore, when the interior of the cell is illuminated with ultraviolet having a wavelength in the vicinity of 220 nm emitted from the light source, only $SO_2$ in the sample gas G is excited and then, the excited $SO_2$ is relaxed to emit fluorescence having a wavelength in the vicinity of 330 nm. The fluorescence having a wavelength in the vicinity of 330 nm selectively passes through the optical filter to detect a fluorescent intensity by a detector and the detected fluorescent intensity is quantified as an numeral using a calibration curve prepared in advance, thereby enabling a concentration of $SO_2$ included in automobile emission or the like to be measured and analyzed with a high precision in a state where no interferential influence is exerted by NO, $H_2O$ or the like included in the sample gas G.

Incidentally, in Table 1, there are shown interferential influence values due to various kinds of gases included in a sample gas G when $O_3$ is added and interferential influence values due to NO in a sample gas G when no $O_3$ is added (in value expressed in terms of $SO_2$ output), and when $O_3$ is added, an interferential influence value equal to or less than a detection limit was obtained on any of a gas component included. It is also clearly shown in Table 1 that an interferential influence caused by NO, which is the largest interferential component in measurement of an $SO_2$ concentration using ultraviolet fluorescence when $O_3$ is added is equal to or less than the detection limit.

TABLE 1

| kind of gas | concentration | result of interferential influence |
|---|---|---|
| Result of interferential influence values when $O_3$ is added ||| 
| NO | 4788 ppm | equal to or less than detection limit |
| $NO_2$ | 228 ppm | equal to or less than detection limit |
| $H_2O$ | 6.53 vol % | equal to or less than detection limit |
| $NH_3$ | 343.7 ppm | equal to or less than detection limit |
| CO | 8.396 vol % | equal to or less than detection limit |
| $CO_2$ | 17.18 vol % | equal to or less than detection limit |
| $C_3H_8$ | 3273 ppm | equal to or less than detection limit |
| $O_2$ | 20.7 vol % | equal to or less than detection limit |
| when $O_3$ is not added ||| 
| NO | 95.66 ppm | 49 ppm(*) |

Figure 2:
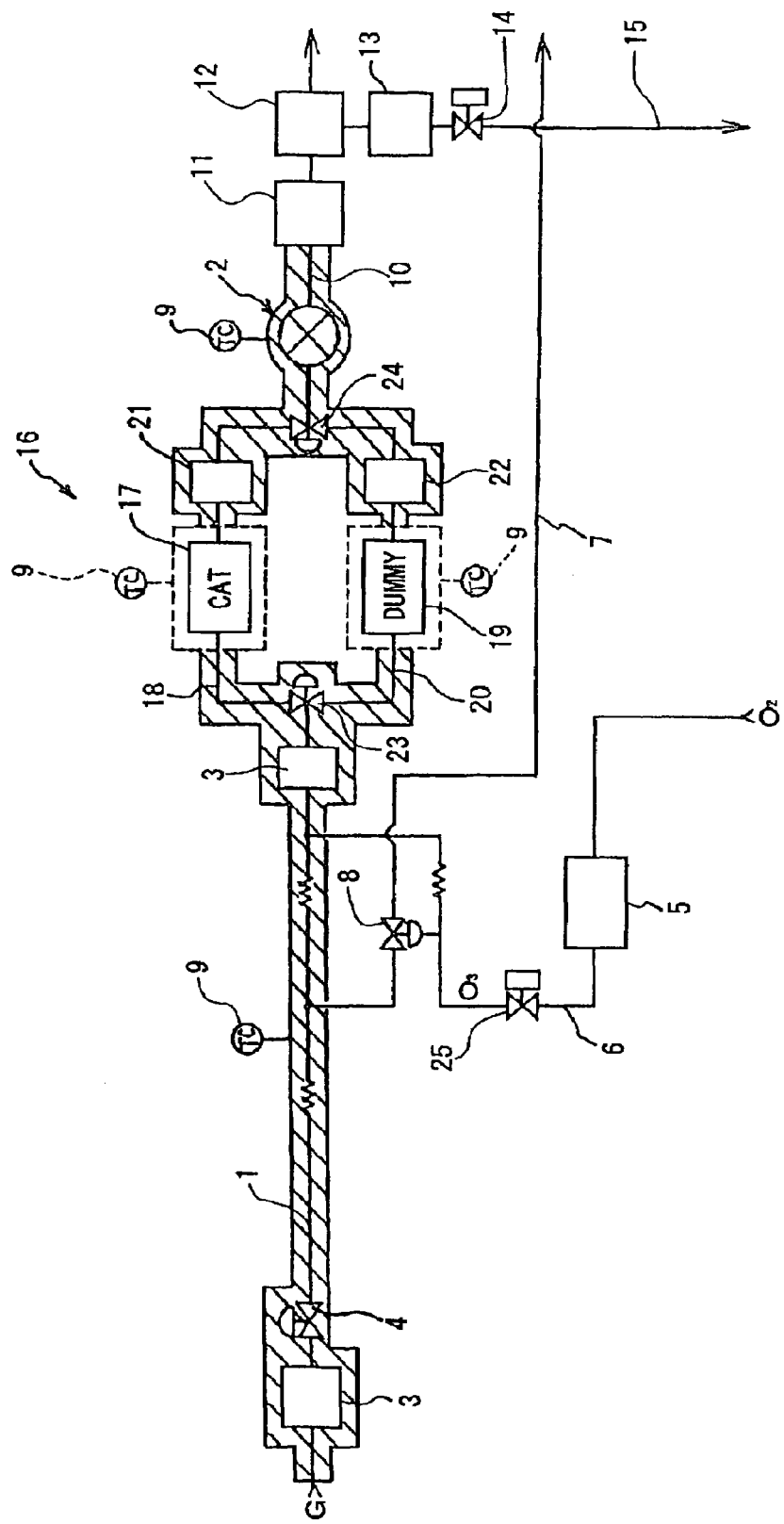
FIG. 2 is a view showing an outline of construction of an analysis apparatus in the entirety according to a second embodiment adopting an analysis method for a sulfur component using ultraviolet fluorescence pertaining to the invention.

FIG. 2 is a view showing an outline of construction of an analysis apparatus in the entirety according to a second embodiment adopting an analysis method for a sulfur component using ultraviolet fluorescence pertaining to the invention. In the analysis apparatus according to the second embodiment, the construction is the same as in the first embodiment with the exception that a pretreatment section 16 described below is provided just before the ultraviolet fluorometric analyzer 2 and the same symbols are attached to the corresponding constituents.

The pretreatment section 16 includes: a quartz tube 17 having an oxidation catalyst (CAT) made from a ceramic such as vanadium pentoxide or mulite ($Al_2O_3/SiO_2$) with a high content of silicon oxide ($SiO_2$) therein; a filter 21; a first gas line 18 constructed so as to control a heating temperature of the quartz tube 17 at a temperature of the order of 400° C.; a dummy pipe 19; a filter 22; a second gas line 20 so as to control a heating temperature of the dummy pipe 19 at a temperature of the order in the range of from 80 to 90° C.; and two valves 23 and 24 capable of changing over between flows of the sample gas G into the first and second gas lines 18 and 20.

In a case where the analysis apparatus of the second embodiment constructed as described above is used to measure and analyze concentrations of sulfur components such as $SO_2$ and others included in the sample gas G using ultraviolet fluorescence, if the valves 23 and 24 are changed over in order to cause the sample gas G to flow in the first gas line 18 of the pretreatment section 16, sulfur compounds such as $H_2S$ and $CS_2$ in the sample gas are oxidized to $SO_2$ while the sample gas G passes through the quartz tube 17 and then introduced into the cell of the ultraviolet fluorometric analyzer 2, where a concentration of all the sulfur components in the sample gas are measured. While if the valves 23 and 24 are changed over in order to cause the sample gas G to flow in the second gas line 20 of the pretreatment section 16, sulfur compounds such as $H_2S$ and $CS_2$ in the sample gas are not oxidized to $SO_2$ while the sample gas G passes through the dummy pipe 19 and, as they are, introduced into the cell of the ultraviolet fluorometric analyzer 2, where a concentration of only $SO_2$ in the sample gas is measured. That is, only by changing over between the first and second lines 18 and 20 in the pretreatment section 16, the apparatus can be used changing over between the two kinds of measurement of a concentration of all the sulfur components in the sample gas and a concentration of only $SO_2$ in the sample gas at any time with simplicity.

Incidentally, in Table 2, there are shown relative sensitivities when each of various kinds of sulfur compounds such as $H_2S$ and $CS_2$ is measured using the first gas line 18 and the values of the sensitivities, when that of $SO_2$ as a reference (1.0) is used, are 0.9 or larger on all sulfur components: it is clear from Table 2 that a measurement precision is high for all the sulfur components.

TABLE 2

Result of relative sensitivity of each sulfur compound

| name of compound | relative sensitivity |
|---|---|
| $SO_2$ | 1.00 |
| $H_2S$ | 0.99 |
| $CS_2$ | 1.00 |
| $CH_3SH$ | 0.98 |
| $C_4H_4S$ | 1.00 |
| $(CH_3)_2S$ | 1.00 |
| $(C_2H_5)_2S$ | 1.00 |
| COS | 0.91 |

Note that while in the above described embodiments, a means in which $O_3$ is added and mixed into the sample gas G is used as a means to oxidize NO to $NO_2$, another construction may be adopted in which $O_2$ is added into the sample gas G, which is illuminated with ultraviolet from the light source of the ultraviolet fluorometric analyzer 2, thereby oxidizing NO in the sample gas G to $NO_2$.

Figure 3:
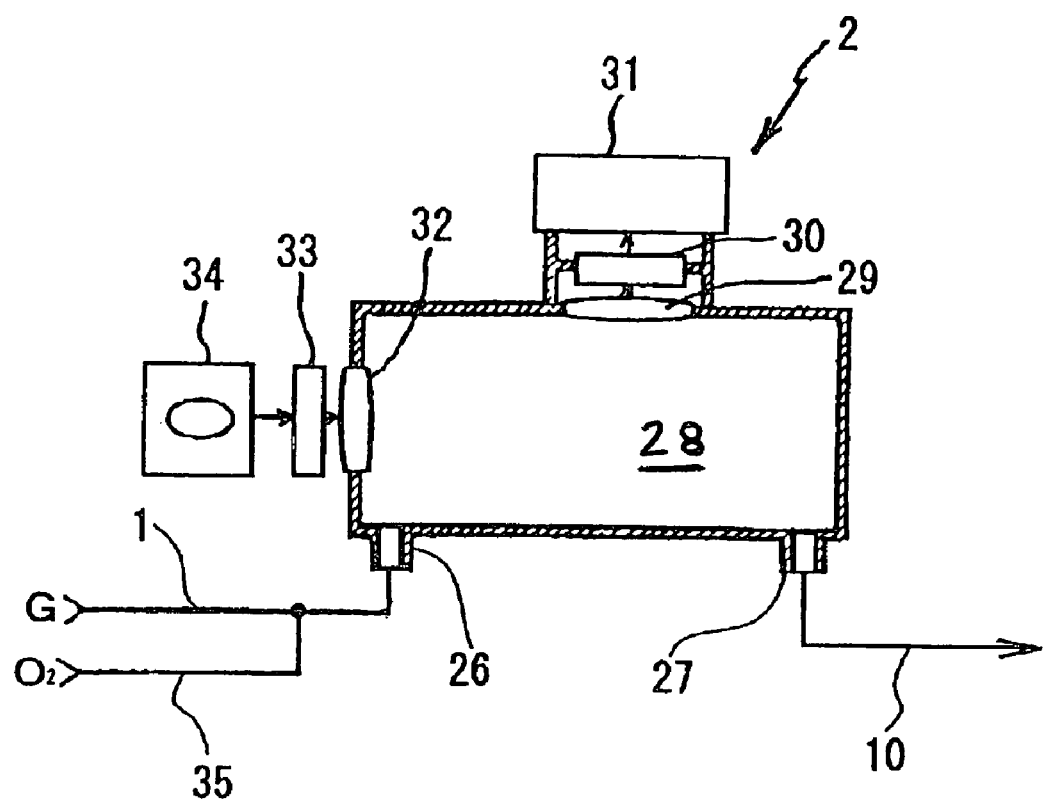
FIG. 3 is an enlarged sectional view showing a main part structure of construction of an analysis apparatus according to a third embodiment adopting an analysis method for a sulfur component using ultraviolet fluorescence pertaining to the invention.

FIG. 3, which shows detailed structure of the above construction, is a sectional view of the vicinity of the ultraviolet fluorometric analyzer 2, and in a sample chamber (cell) 28 having an introducing section 26 and a discharging section 27 for the sample gas G, there is integrally provided, as a single piece therewith, a detector 31 such as a photodiode selecting only fluorescence having a wavelength in the vicinity of 330 nm emitted from $SO_2$ through a fluorecence collective lens 29 and through an optical filter 30 to detect an intensity thereof; in addition, sideways to the outside of the cell 28 in the sample gas introducing section 26 side, there is installed an ultraviolet lamp (light source) 34 emitting ultraviolet directed to the sample gas in the cell 28 through excitation collective lens 32 and through an optical filter 33; and to a site close to the sample gas introducing section 26 of the introducing pipe 1, there is communication-connected an $O_2$ supply pipe 35.

In an analysis apparatus for a sulfur component using ultraviolet fluorescence, constructed as shown in FIG. 3, the sample gas G added and mixed with $O_2$ at a given ratio through the supply pipe 35 is introduced into the cell 28 through the introducing section 26 and the $O_2$ mixed sample gas G is illuminated with ultraviolet not only to thereby cause NO in the sample gas G to react with $O_2$ to $NO_2$ in an oxidized form but also to excite $NO_2$ and $SO_2$ in the sample gas G including $NO_2$ obtained by oxidation with the result being emission of fluorescence therefrom. Only fluorescence having a wavelength in the vicinity of 330 nm of all the fluorescence is selectively detected by the detector 31 through the collective lens 29 and the optical filter 30, thereby enabling a fluorescent intensity of $SO_2$, that is a concentration of $SO_2$ to be measured and analyzed with a high precision without receiving an interferential influence caused by NO.

In the second embodiment shown in FIG. 2, by adding a pretreatment apparatus such as a scrubber for $SO_2$ to a gas introducing section to the cell of ultraviolet fluorometric analyzer 2, a concentration of sulfur components except for $SO_2$ can be measured when the first gas line 18 is used by changeover and furthermore, by adding another pretreatment apparatus using active charcoal or a high temperature furnace at 1000° C. or higher, a concentration of $SO_3$ or the like can also be measured.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An analysis apparatus for a sulfur component using ultraviolet fluorescence, which includes an introducing pipe for a sample gas; and an ultraviolet fluorometric analyzer, connected to the introducing pipe, and illuminating the sample gas with ultraviolet to detect fluorescence emitted accompanying the illumination and to thereby measure concentrations of sulfur components including at least $SO_2$ in the sample gas, the apparatus further comprising:

means for oxidizing NO, which is an interferential component in the sample gas, to $NO_2$ installed part way downstream from an inlet end of the introducing pipe;

a pretreatment section having a first gas line and a second gas line and a valve changing over between flows of the sample gas into the first and second gas lines provided downstream of the means for oxidizing NO and immediately prior to the ultraviolet fluorometric analyzer; and means for oxidizing a sulfur compound in the sample gas to $SO_2$ provided in the first gas line, wherein the second gas line provides any flow of sample gas to the ultraviolet fluorometric analyzer without oxidizing sulfur compounds to $SO_2$.

2. The analysis apparatus for a sulfur component using ultraviolet fluorescence according to claim 1, wherein the means for oxidizing NO to $NO_2$ is a means for adding ozone into the sample gas flowing in the introducing pipe.

3. The analysis apparatus for a sulfur component using ultraviolet fluorescence according to claim 2 further comprising:

heating means for heating to and holding at a temperature in the introducing pipe of the sample gas and the sample chamber of the ultraviolet fluorometric analyzer in the range where essentially no condensation in the sample occurs.

4. The analysis apparatus for a sulfur component using ultraviolet fluorescence according to claim 1, farther comprising:

heating means for heating to and holding at a temperature in the introducing pipe of the sample gas and the sample chamber of the ultraviolet fluorometric analyzer in the range where essentially no condensation in the sample occurs.

5. An analysis apparatus for a sulfur component using ultraviolet fluorescence, the apparatus comprising:

an introducing pipe for a sample gas;

an ultraviolet fluorometric analyzer connected to the introducing pipe, and illuminating the sample gas with ultraviolet to detect fluorescence emitted accompanying the illumination and to thereby measure concentrations of sulfur components including at least $SO_2$ in the sample gas;

an oxidizer for oxidizing NO, which is an interferential component in the sample gas, to $NO_2$ installed part way downstream from an inlet end of the introducing pipe; and a pretreatment section located downstream of the oxidizer for oxidizing NO and immediately prior to the ultraviolet fluorometric analyzer, the pretreatment section having a first gas line and a second gas line and a valve changing over between flows of the sample gas into the first and second gas lines; and an oxidation catalyst for oxidizing a sulfur compound in the sample gas to $SO_2$ provided in the first gas line, wherein the second gas line provides any flow of sample gas to the ultraviolet fluorometric analyzer without oxidizing sulfur compounds to $SO_2$.

6. The analysis apparatus for a sulfur component using ultraviolet fluorescence according to claim 5 further comprising:

heating means for heating to and holding at a temperature in the introducing pipe of the sample gas and the sample chamber of the ultraviolet fluorometric analyzer in the range where essentially no condensation in the sample occurs.

7. An apparatus for analyzing sulfur components, including sulfur dioxide, in a sample gas using ultraviolet fluorescence, comprising:

an introducing pipe for introducing a sample gas;

an ultraviolet fluorometric analyzer for detecting the sulfur components connected to the introducing pipe;

a pretreatment section provided upstream of the fluorometric analyzer, the pretreatment section having a first gas line and a second gas line, each of the gas lines being communication-connected to the introducing pipe and to the ultraviolet fluorometric analyzer, with the first gas line being provided with means for oxidizing the sulfur components other than sulfur dioxide in the sample gas to sulfur dioxide, the pretreatment section further having a valve for changing over flows of the sample gas into the first or second gas lines; and means for oxidizing nitrogen monoxide to nitrogen dioxide in the sample gas before detecting the sulfur components.

8. The apparatus of claim 7 wherein the means for oxidizing nitrogen monoxide to nitrogen dioxide is a means for adding ozone into the sample gas flowing in the introducing pipe.

9. The apparatus of claim 8 further comprising:

heating means for heating to and holding at a temperature in the introducing pipe of the sample gas and the sample chamber of the ultraviolet fluorometric analyzer in the range where essentially no condensation in the sample occurs.

10. The apparatus of claim 7 further comprising:

heating means for heating to and holding at a temperature in the introducing pipe of the sample gas and the sample chamber of the ultraviolet fluorometric analyzer in the range where essentially no condensation in the sample occurs.

11. A method for analyzing sulfur components, including sulfur dioxide, in a sample gas containing nitrogen monoxide comprising:

providing an introducing pipe for introducing a sample gas;

providing an ultraviolet fluorometric analyzer for detecting the sulfur components connected to the introducing pipe;

providing a pretreatment section upstream of the fluorometric analyzer, the pretreatment section having a first gas line and a second gas line, each of the gas lines being communication-connected to the introducing pipe and to the ultraviolet fluorometric analyzer, with the first gas line being provided with means for oxidizing the sulfur components other than sulfur dioxide in the sample gas to sulfur dioxide, the pretreatment section further having a valve for changing over flows of the sample gas into the first or second gas lines;

oxidizing nitrogen monoxide to nitrogen dioxide in the sample gas before detecting the sulfur components;

illuminating the sample gas with ultraviolet light and detecting a fluorescence to measure the sulfur components, including sulfur dioxide;

determining a concentration of all sulfur components in the sample gas by oxidizing the components other than sulfur dioxide in the sample gas to sulfur dioxide before detecting of fluorescence; and determining a concentration of sulfur dioxide only in the sample gas by detecting of fluorescence.

12. The method of claim 11 further comprising: oxidizing nitrogen monoxide to nitrogen dioxide by adding ozone into the sample gas.

13. The method of claim 11 further comprising:

heating to and holding at a temperature in the introducing pipe of the sample gas and the sample chamber of the ultraviolet fluorometric analyzer in the range where essentially no condensation in the sample occurs.

* * * * *

UNITED STATES PATENT AND TRADEMARK OFFICE
CERTIFICATE OF CORRECTION

PATENT NO. : 7,427,378 B2
APPLICATION NO. : 10/917903
DATED : September 23, 2008
INVENTOR(S) : Kotaro Akashi et al.

It is certified that error appears in the above-identified patent and that said Letters Patent is hereby corrected as shown below:

Column 8, Line 52, Claim 4:

Delete "farther" and insert --further--

Signed and Sealed this

Twentieth Day of October, 2009

David J. Kappos
*Director of the United States Patent and Trademark Office*